(12) United States Patent
Gysling et al.

(10) Patent No.: US 7,389,687 B2
(45) Date of Patent: *Jun. 24, 2008

(54) SYSTEM FOR MEASURING A PARAMETER OF AN AERATED MULTI-PHASE MIXTURE FLOWING IN A PIPE

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 206 days.

This patent is subject to a terminal disclaimer.

(21) Appl. No.: 11/268,815

(22) Filed: Nov. 7, 2005

(65) Prior Publication Data

US 2006/0096388 A1 May 11, 2006

Related U.S. Application Data

(60) Provisional application No. 60/625,498, filed on Nov. 5, 2004.

(51) Int. Cl.
*G01F 15/08* (2006.01)
(52) U.S. Cl. .......................................... 73/200
(58) Field of Classification Search .............. 73/861.04, 73/861.08, 861.18, 32, 61.44, 200
See application file for complete search history.

(56) References Cited

U.S. PATENT DOCUMENTS

| | | | |
|---|---|---|---|
| 2,874,568 A | 2/1959 | Petermann | |
| 3,444,723 A | 5/1969 | Wakefield | |
| 3,780,577 A | 12/1973 | Brown | |
| 4,004,461 A | 1/1977 | Lynnworth | |
| 4,048,853 A | 9/1977 | Smith et al. | |
| 4,080,837 A | 3/1978 | Alexander et al. | |
| 4,144,754 A | 3/1979 | Pitts et al. | |
| 4,195,517 A | 4/1980 | Kalinoski et al. | |
| 4,248,085 A | 2/1981 | Coulthard | |
| 4,262,523 A | 4/1981 | Stansfeld | |
| 4,445,389 A | 5/1984 | Potzick et al. | |
| 4,580,444 A | 4/1986 | Abts et al. | |
| 4,773,257 A | 9/1988 | Aslesen et al. | |

(Continued)

FOREIGN PATENT DOCUMENTS

GB 2009931 6/1979

(Continued)

OTHER PUBLICATIONS

"Polymer Piezoelectric Transducers for Ultrasonic NDE" Aughors: Yoseph Bar-Cohen, Tianji Xue and Shyh-Shiuh Lih.

(Continued)

*Primary Examiner*—Jewel Thompson
(74) *Attorney, Agent, or Firm*—Michael Grillo

(57) ABSTRACT

A method and apparatus for measuring at least one characteristic of an aerated fluid flowing within a pipe is provided, wherein the method includes generating a measured sound speed, a measured density, a pressure and a gas volume fraction for the aerated fluid. The method also includes correcting the measured density responsive to the measured sound speed, the pressure and the gas volume fraction to generate a corrected density. The method further includes calculating a liquid phase density, determining whether the gas volume fraction is above a predetermined threshold value and generating a mass flow rate responsive to whether the gas volume fraction is above the predetermined threshold value.

21 Claims, 14 Drawing Sheets

U.S. PATENT DOCUMENTS

| | | | |
|---|---|---|---|
| 4,823,613 A | 4/1989 | Cage et al. |
| 4,896,540 A | 1/1990 | Shakkottai et al. |
| 4,972,724 A | 11/1990 | Ricken |
| 5,029,482 A | 7/1991 | Liu et al. |
| 5,040,415 A | 8/1991 | Barkhoudarian |
| 5,048,349 A | 9/1991 | Wolff |
| 5,083,452 A | 1/1992 | Hope |
| 5,218,197 A | 6/1993 | Carroll |
| 5,224,372 A | 7/1993 | Kolpak |
| 5,259,239 A | 11/1993 | Gaisford |
| 5,285,675 A | 2/1994 | Colgate et al. |
| 5,367,911 A | 11/1994 | Jewell et al. |
| 5,398,542 A | 3/1995 | Vasbinder |
| 5,488,870 A | 2/1996 | Yoshimura et al. |
| 5,524,475 A | 6/1996 | Kolpak et al. |
| 5,526,844 A | 6/1996 | Kamen et al. |
| 5,591,922 A | 1/1997 | Segeral et al. |
| 5,594,180 A | 1/1997 | Carpenter et al. |
| 5,654,502 A | 8/1997 | Dutton |
| 5,741,980 A | 4/1998 | Hill et al. |
| 5,770,805 A | 6/1998 | Castel |
| 5,770,806 A | 6/1998 | Hiismaki |
| 5,827,977 A | 10/1998 | Ortiz et al. |
| 5,835,884 A | 11/1998 | Brown |
| 5,845,033 A | 12/1998 | Berthold et al. |
| 5,856,622 A | 1/1999 | Yamamoto et al. |
| 5,948,959 A | 9/1999 | Peloquin |
| 6,016,702 A | 1/2000 | Maron |
| 6,065,328 A | 5/2000 | Dayton et al. |
| 6,151,958 A | 11/2000 | Letton et al. |
| 6,202,494 B1 | 3/2001 | Riebel et al. |
| 6,209,388 B1 | 4/2001 | Letton et al. |
| 6,318,156 B1 | 11/2001 | Dutton et al. |
| 6,335,959 B1 | 1/2002 | Lynch et al. |
| 6,354,147 B1 | 3/2002 | Gysling et al. |
| 6,378,357 B1 | 4/2002 | Han et al. |
| 6,397,683 B1 | 6/2002 | Hagenmeyer et al. |
| 6,401,538 B1 | 6/2002 | Han et al. |
| 6,422,092 B1 | 7/2002 | Morrison et al. |
| 6,435,030 B1 | 8/2002 | Gysling et al. |
| 6,443,226 B1 | 9/2002 | Diener et al. |
| 6,450,037 B1 | 9/2002 | McGuinn et al. |
| 6,463,813 B1 | 10/2002 | Gysling |
| 6,502,456 B1 | 1/2003 | Chen |
| 6,502,465 B1 | 1/2003 | Vedapuri et al. |
| 6,502,466 B1 | 1/2003 | Cage et al. |
| 6,532,827 B1 | 3/2003 | Ohnishi |
| 6,536,291 B1 | 3/2003 | Gysling et al. |
| 6,550,342 B2 | 4/2003 | Croteau et al. |
| 6,558,036 B2 | 5/2003 | Gysling et al. |
| 6,575,043 B1 | 6/2003 | Huang et al. |
| 6,587,798 B2 | 7/2003 | Kersey et al. |
| 6,601,458 B1 | 8/2003 | Gysling et al. |
| 6,609,069 B2 | 8/2003 | Gysling |
| 6,672,163 B2 | 1/2004 | Han et al. |
| 6,691,584 B2 | 2/2004 | Gysling et al. |
| 6,698,297 B2 | 3/2004 | Gysling |
| 6,732,575 B2 | 5/2004 | Gysling et al. |
| 6,745,135 B2 | 6/2004 | Keilty et al. |
| 6,763,698 B2 | 7/2004 | Greenwood |
| 6,776,054 B1 | 8/2004 | Stephenson et al. |
| 6,782,150 B2 | 8/2004 | Davis et al. |
| 6,802,224 B2 | 10/2004 | Nakao et al. |
| 6,813,962 B2 | 11/2004 | Gysling et al. |
| 6,817,229 B2 | 11/2004 | Han et al. |
| 6,837,098 B2 | 1/2005 | Gysling et al. |
| 6,862,920 B2 | 3/2005 | Gysling et al. |
| 6,868,737 B2 | 3/2005 | Croteau et al. |
| 6,889,562 B2 | 5/2005 | Gysling et al. |
| 6,898,541 B2 | 5/2005 | Gysling et al. |
| 6,945,095 B2 | 9/2005 | Johansen |
| 6,950,760 B2 | 9/2005 | Henry et al. |
| 6,971,259 B2 | 12/2005 | Gysling |
| 6,988,411 B2 | 1/2006 | Gysling et al. |
| 7,013,715 B2 | 3/2006 | Dutton et al. |
| 7,040,181 B2 | 5/2006 | Rieder et al. |
| 7,059,199 B2 | 6/2006 | Mattar et al. |
| 7,086,278 B2 | 8/2006 | Gysling et al. |
| 7,096,719 B2 | 8/2006 | Gysling |
| 7,134,320 B2 * | 11/2006 | Gysling et al. ............... 73/32 A |
| 7,152,460 B2 | 12/2006 | Gysling et al. |
| 2001/0045134 A1 | 11/2001 | Henry et al. |
| 2002/0095263 A1 | 7/2002 | Gysling et al. |
| 2002/0123852 A1 | 9/2002 | Gysling et al. |
| 2002/0129662 A1 | 9/2002 | Gysling et al. |
| 2003/0038231 A1 | 2/2003 | Gysling et al. |
| 2003/0089161 A1 | 5/2003 | Gysling |
| 2003/0136186 A1 | 7/2003 | Gysling et al. |
| 2003/0154036 A1 | 8/2003 | Gysling et al. |
| 2004/0016284 A1 | 1/2004 | Gysling et al. |
| 2004/0069069 A1 | 4/2004 | Croteau |
| 2004/0074312 A1 | 4/2004 | Gysling |
| 2004/0100883 A1 | 5/2004 | Sakagami |
| 2004/0107144 A1 | 6/2004 | Gysling |
| 2004/0139791 A1 | 7/2004 | Johansen |
| 2004/0144182 A1 | 7/2004 | Gysling et al. |
| 2004/0167735 A1 | 8/2004 | Gysling et al. |
| 2004/0168522 A1 | 9/2004 | Fernald et al. |
| 2004/0168523 A1 | 9/2004 | Fernald |
| 2004/0173010 A1 | 9/2004 | Gysling et al. |
| 2004/0194539 A1 | 10/2004 | Gysling et al. |
| 2004/0199340 A1 | 10/2004 | Gysling et al. |
| 2004/0199341 A1 | 10/2004 | Gysling et al. |
| 2004/0210404 A1 | 10/2004 | Gysling et al. |
| 2004/0216509 A1 | 11/2004 | Antonijevic |
| 2004/0226386 A1 | 11/2004 | Croteau et al. |
| 2004/0231431 A1 | 11/2004 | Bailey et al. |
| 2004/0255695 A1 | 12/2004 | Gysling et al. |
| 2005/0005711 A1 | 1/2005 | Gysling et al. |
| 2005/0011283 A1 | 1/2005 | Gysling et al. |
| 2005/0011284 A1 | 1/2005 | Davis et al. |
| 2005/0039520 A1 | 2/2005 | Bailey et al. |
| 2005/0044929 A1 | 3/2005 | Gysling et al. |
| 2005/0044966 A1 | 3/2005 | Croteau et al. |
| 2005/0050956 A1 | 3/2005 | Croteau et al. |
| 2005/0061060 A1 | 3/2005 | Banach et al. |
| 2005/0072216 A1 | 4/2005 | Engle |
| 2005/0120799 A1 | 6/2005 | Gysling et al. |
| 2005/0138993 A1 | 6/2005 | Mattar et al. |
| 2005/0171710 A1 | 8/2005 | Gysling et al. |
| 2005/0188771 A1 | 9/2005 | Lund Bo et al. |
| 2005/0193832 A1 | 9/2005 | Tombs et al. |
| 2005/0210965 A1 | 9/2005 | Sinha |
| 2006/0156831 A1 | 7/2006 | Rieder et al. |
| 2006/0169058 A1 | 8/2006 | Gysling et al. |

FOREIGN PATENT DOCUMENTS

| | | |
|---|---|---|
| GB | 2282931 | 4/1995 |
| WO | WO 04065912 | 8/2004 |
| WO | WO 05010470 | 2/2005 |

OTHER PUBLICATIONS

"Piezoelectric Polymers" ICASE Report No. 2001-43 - Dec. 2001.

"Piezo Film Sensors Technical Manual" P/N 1005663-1 Rev. B Apr. 2, 1999.

Sonar-Based Volumetric Flow Meter For Pulp and Paper Applications - Daniel L. Gysling & Douglas H. Loose - Dec. 12, 2003.

Sonar-Based Volumetric Flow Meter for Chemical and Petrochemical Applications - Daniel L. Gysling & Douglas H. Loose - Feb. 14, 2003.

New Flowmeter Principle - By Walt Boyes - Flow Control Magazine - Oct. 2003 Issue.

SONAR Gets into the Flow - Daniel L. Gysling and Douglas H. Loose - Modern Process - Jan. 2004.

"Noise and Vibration Control Principles and Applications", Leo L. Beranek and Istvan L. Ver, A. Wiley Interscience Publication, pp. 537-541, Aug. 1992.

"Two Decades of Array Signal Processing Research, The Parametric Approach", H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attentuation of Acoustic Waves in Suspensions" by R.L. Gibson, Jr. and M.N. Toksoz.

Nyfors Ebbe et al: Mixtures of Oil, Water, and Gas with Microwave Sensors. New Developments and Field Experience of the MFI MultiPhase, and WaterCut Meters of Roxar, Proc Spie Int Soc Opt Eng: Proceedings of Spie - The International Society for Optical Engineering 200 Society of Photo-Optical Instrumentation Engineers, Bellinghma, WA, USA, vol. 4129, 2000, pp. 12-21, XP002402006 - Paragraphs [02.4], [04.1].

Mehdizadeh P: "Test Verifies Water-0Cut Meter Accuracy in SteamFlood" Oil and Gas Journal, Pennwell, Houston, TX, US, vol. 98, No. 40, Oct. 2, 2000 - pp. 97-98, 100 XP000968244, issn: 0030-1388 - Figure 2.

"PVDF and Array Transducers" Author: Robert A. Day - NDTnet - Sep. 1996 - vol. No. 9.

* cited by examiner

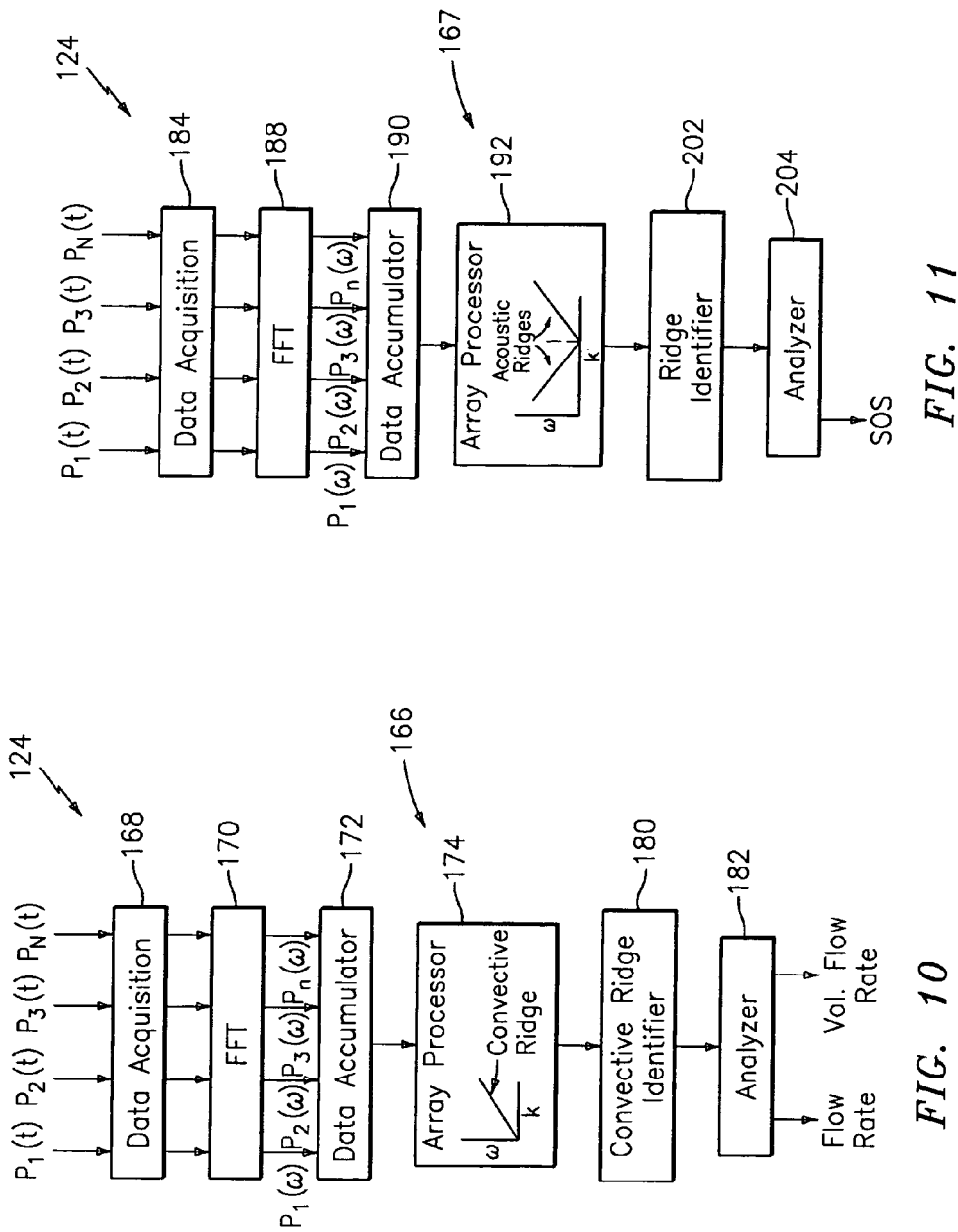

SYSTEM FOR MEASURING A PARAMETER OF AN AERATED MULTI-PHASE MIXTURE FLOWING IN A PIPE

CROSS-REFERENCE TO RELATED APPLICATIONS

The present invention claims the benefit of U.S. Provisional Patent Application Ser. No. 60/625,498 filed Nov. 5, 2004, which is incorporated herein by reference.

TECHNICAL FIELD

This invention relates generally to measuring multi-phase mixtures flowing in a pipe, and more particularly to a system for measuring an aerated multi-phase mixture flowing in a pipe.

BACKGROUND

Metering well head production rates is a long standing challenge for the oil and gas industry. Performing accurate and timely monitoring of the production rates has many benefits, which include optimizing overall field and specific well production.

Well head monitoring represents a difficult technical challenge. The difficulty is due in no small part to the extreme variability of produced fluids which can include various types and mixtures of oil, water, gas, and solid particles.

Many companies have developed various types of three phase meters design to address the well head flow metering market. These products have met relatively limited commercial success due to a combination of performance, accuracy, and cost issues. This disclosure provide an means and apparatus for well head monitoring that combines multiple existing technologies in to system that should met a wide range of cost and performance goals.

SUMMARY OF THE INVENTION

A flow measuring system for measuring a characteristic of a fluid flowing within a pipe is provided and includes a density meter having at least one tube, wherein fluid flows therethrough and wherein the density meter provides a signal indicative of at least one of a measured mass flow rate and a measured density of the fluid. A flow measuring device for measuring the speed of sound propagating through the fluid is also included and provides at least one of an SOS signal indicative speed of sound propagating through the fluid, GVF signal indicative of the gas volume fraction of the fluid and volumetric flow rate. Moreover, a processing unit is provided for determining a corrected mass flow rate measurement in response to at least one of the SOS signal and the GVF signal and/or determining a corrected density measurement in response to the SOS signal and the GVF signal.

A method for measuring at least one characteristic of an aerated fluid flowing within a pipe is provided, wherein the method includes generating a measured sound speed, a measured density, a pressure and a gas volume fraction for the aerated fluid. The method includes correcting the measured density responsive to the measured sound speed, the pressure and the gas volume fraction to generate a corrected density. The method further includes calculating a liquid phase density, generating a measured a mass flow rate and correcting the measured mass flow rate responsive to the measured sound speed, the pressure and the gas volume fraction to generate a corrected mass flow rate.

A method for measuring at least one characteristic of an aerated fluid flowing within a pipe is provided, wherein the method includes generating a measured sound speed, a measured density, a pressure and a gas volume fraction for the aerated fluid. The method also includes correcting the measured density responsive to the measured sound speed, the pressure and the gas volume fraction to generate a corrected density. The method further includes calculating a liquid phase density, determining whether the gas volume fraction is above a predetermined threshold value and generating a mass flow rate responsive to whether the gas volume fraction is above the predetermined threshold value.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike:

FIG. 10 is a schematic diagram of a flow logic of an array processor of a flow measuring apparatus in accordance with the present invention;

FIG. 11 is a schematic diagram of a speed of sound (SOS) logic of an array processor of a flow measuring apparatus in accordance with the present invention;

DETAILED DESCRIPTION

Figure 1:
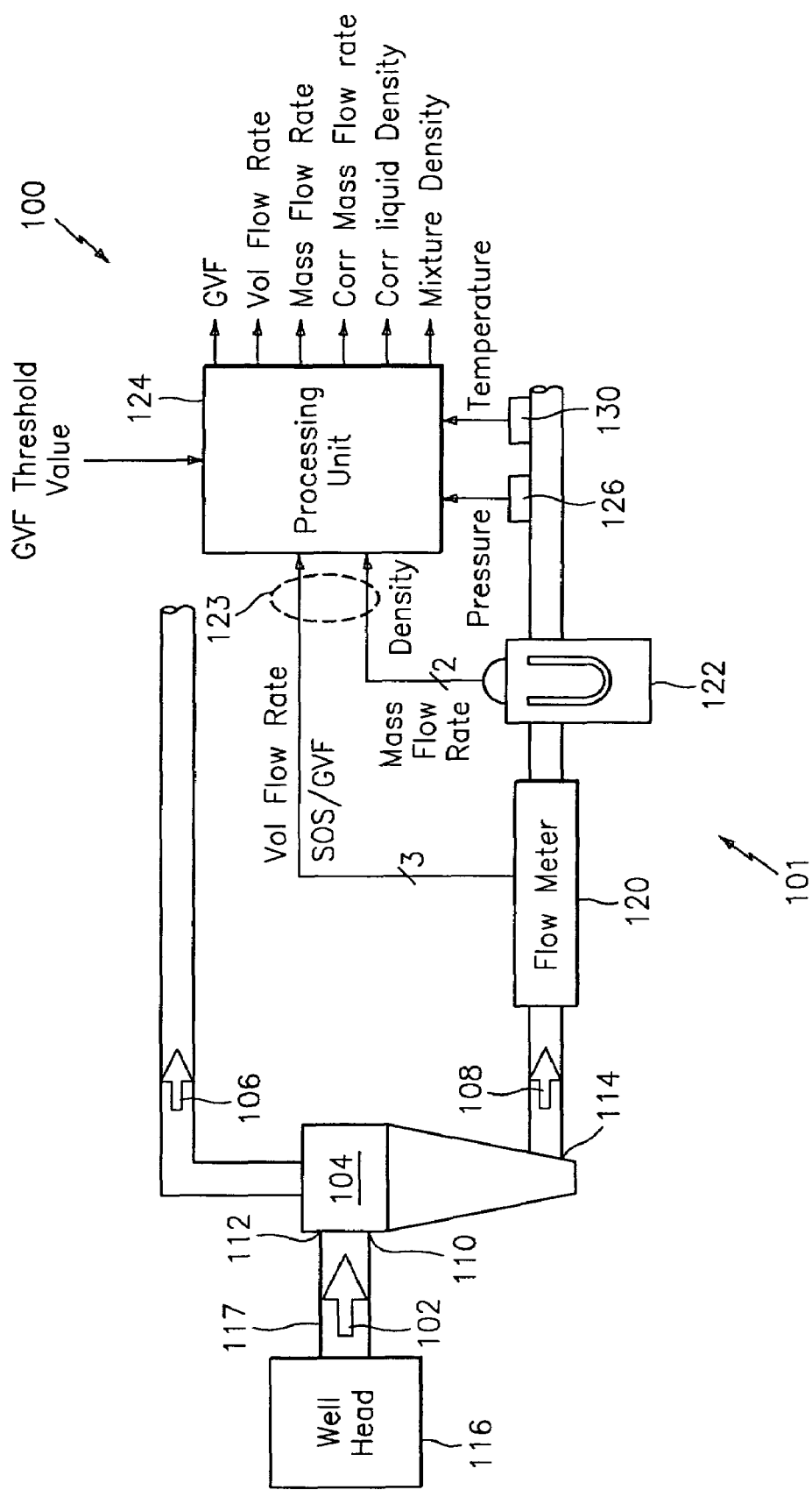
FIG. 1 is a schematic block diagram illustrating one embodiment of a configuration for a well metering system for accurately determining the characteristics of a multiphase production stream, in accordance with the present invention.
Figure 6:
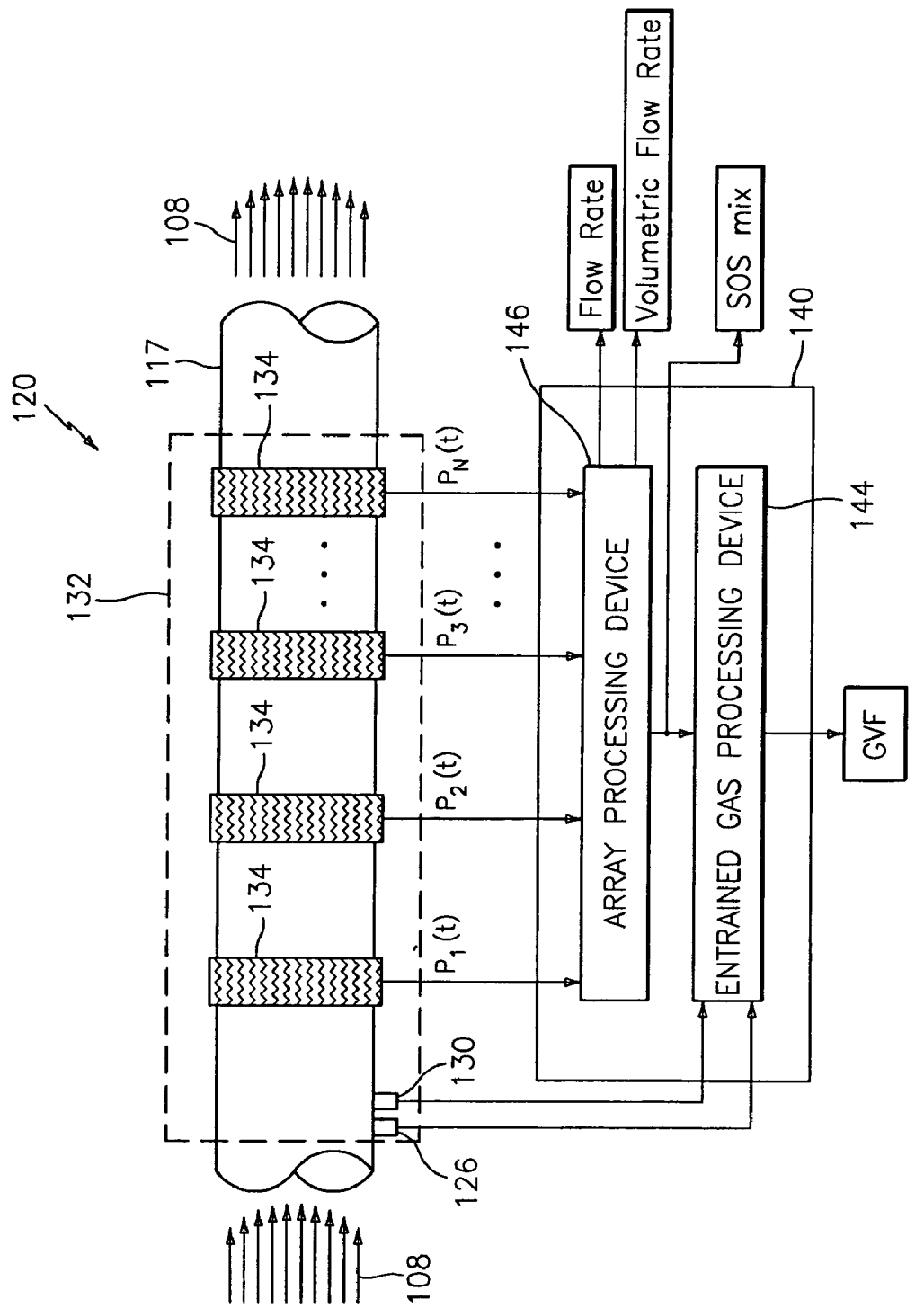
FIG. 6 is a side schematic diagram of a flow meter for the well metering system of FIG. 1.

As shown in FIG. 1, the present invention provides a system 101 for measuring a parameter of an aerated multi-phase fluid flow. The multi-phase fluid flow or mixture 108 includes any gas/liquid(s) mixtures, gas/liquid(s)/solid(s) mixtures flowing through the pipe 14. The system 101 includes a combination of a density meter, such as a coriolis meter, and a flow meter having an array of sensors 134 for measuring various parameters of the fluid mixture, as shown in FIG. 6. The flow meter 120 provides a signal indicative of the speed of sound propagating through a pipe 117, the gas volume fraction of the fluid flow, the velocity of the fluid flow, and/or the volumetric flow rate of the fluid flow. The present invention will be described in the context of a measurement device 101 for a separator device 104 of a well metering system 100, but one will understand and appreciate that the present invention may be used to measure parameters of an aerate multi-phase liquid flowing in any pipe.

Referring to FIG. 1, a schematic block diagram illustrating one embodiment of a configuration for a well metering system 100 for accurately determining the characteristics of a multiphase production stream 102 is shown. The well metering system 100 utilizes a multiphase separator device 104 (e.g. cyclone separator) to separate the production stream 102, which is comprised of a gas/oil/water mixture, into a first fluid flow 106 and a second fluid flow 108, wherein the first fluid flow 106 is comprised of mostly a gas and the second fluid flow 108 is comprised mostly of a liquid. The multiphase separator device 104 includes a separator device process flow inlet 110, a separator device gas outlet 112 and a separator device liquid outlet 114, wherein the separator device process flow inlet 110 is in flow communication with a production stream source (hereinafter "well head") 116 via a pipe, duct or other form of conduit (hereinafter "pipe") 112 for receiving the production stream 102.

The well metering system 100 also includes flow meter 120 having an array of sensors disposed axially-spaced along the pipe 117. The flow meter 120 is disposed downstream of the separator device liquid outlet 114 for measuring the second fluid flow 108. Furthermore, the well metering system 100 includes a density meter, such as a Coriolis meter 122, disposed in flow communication with the pipe 117 for receiving the second fluid flow 108. The density meter 122 is shown disposed downstream from the flow meter 120, but it is contemplated that the density meter may be disposed upstream of the flow meter. A processing device 124 is also provided, wherein the processing device 124 is associated with the flow meter 120 and the density meter 122 for receiving data therefrom.

Figure 9:
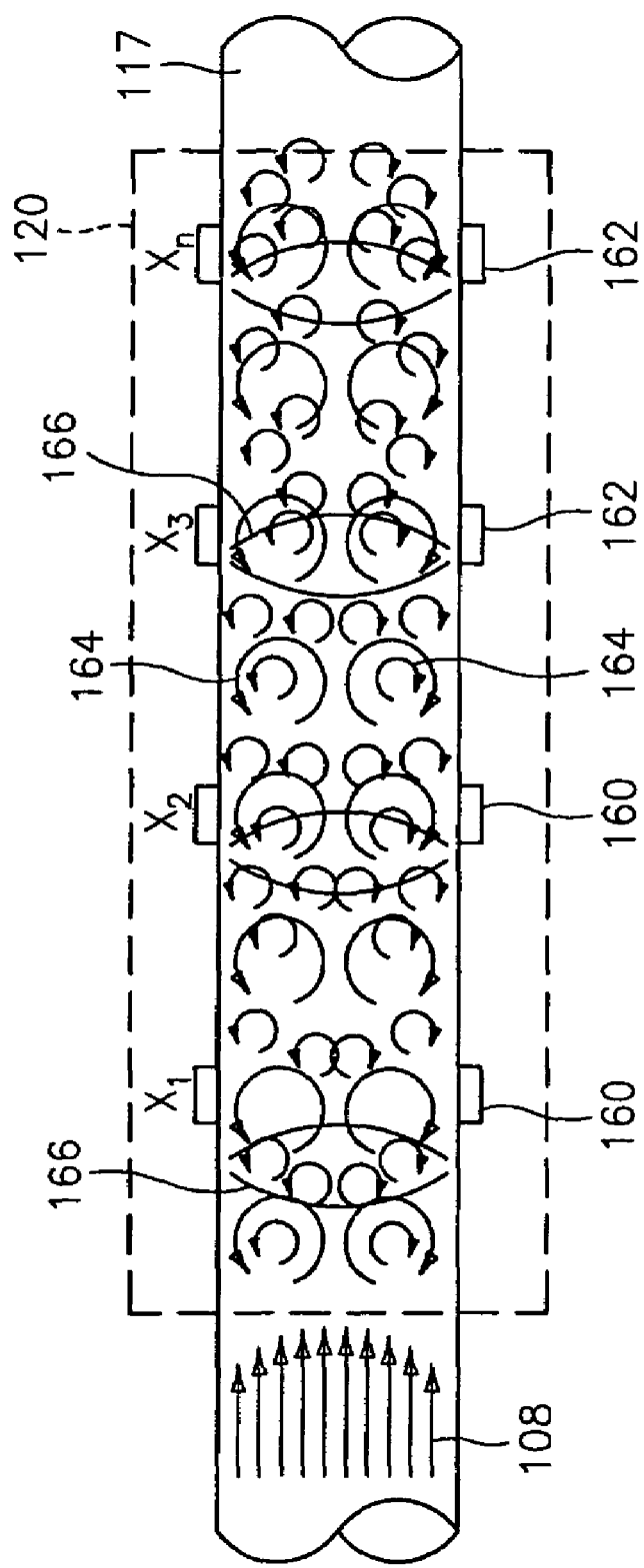
FIG. 9 is a cross-sectional view of a pipe having a turbulent fluid flow or mixture flowing therein, the flow having coherent structures therein, namely acoustic waves and vortical disturbances.

The flow meter 120, in accordance with the present invention, can determine the speed at which sound (i.e., acoustic wave 166 in FIG. 9) propagates through the fluid flow 108 within the pipe 117 to measure particular characteristics of the multi-phase fluid flows. The apparatus may also determine the speed at which pressure disturbances propagate through the pipe 117 to determine the velocity of the fluid flow 108. The pressure disturbances 164 may be in the form of vortical disturbances 88 (e.g., turbulent eddies 164 in FIG. 9) or other pressure disturbances that convect (or propagate) with the flow.

Referring to FIG. 6, the flow meter 120 includes an array of strain-based sensors or pressure sensors 134 for measuring the unsteady pressures produced by vortical disturbances within the pipe and speed of sound propagating through the flow, which are indicative of parameters and/or characteristics of the fluid flow 108. The pressure signals $P_1(t)$-$P_N(t)$ are provided to the processing unit 140, which digitizes the signals and computes the appropriate flow parameter(s).

The array of pressure sensors 134 comprises an array of at least two pressure sensors spaced axially along the outer surface of the pipe 117, having a fluid flow 108 propagating therein. The pressure sensors 134 may be clamped onto or generally removably mounted to the pipe by any releasable fastener, such as bolts, screws and clamps. Alternatively, the sensors may be permanently attached to or integral (e.g., embedded) with the pipe 117. The array of sensors 134 may include any number of pressure sensors greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desire update rate of the output parameter provided by the flow meter 120. The pressure sensors 134 measure the unsteady pressures produced by acoustic waves 166 propagating through the flow and pressure disturbances 164 (e.g., vortical eddies) that convect with the flow within the pipe 117, which are indicative of the speed of sound (SOS) propagating through the fluid flow 108 in the pipe and the velocity of disturbances propagating through the flow 108, respectively. The output signals ($P_1(t)$-$P_N(t)$) of the pressure sensors 134 are provided to a signal amplifier that amplifies the signals generated by the pressure sensors 134. The processing unit 140 processes the pressure measurement data $P_1(t)$-$P_N(t)$ and determines the desired parameters and characteristics of the flow 108, as described hereinbefore.

The density meter 122 measures and generates data responsive to the mass flow and the density of the fluid flow 108. The flow meter 120 and the Coriolis meter 122 then communicate the second flow meter data and the density data, respectively, to the processing device 124 as shown in FIG. 1. The processing device 124 then processes these inputs to determine gas volume fraction, mixture velocity, volumetric flow rate, mass flow rate, corrected mass flow rate, corrected liquid density, and corrected mixture density, as described in more detail hereinafter.

Figure 2:
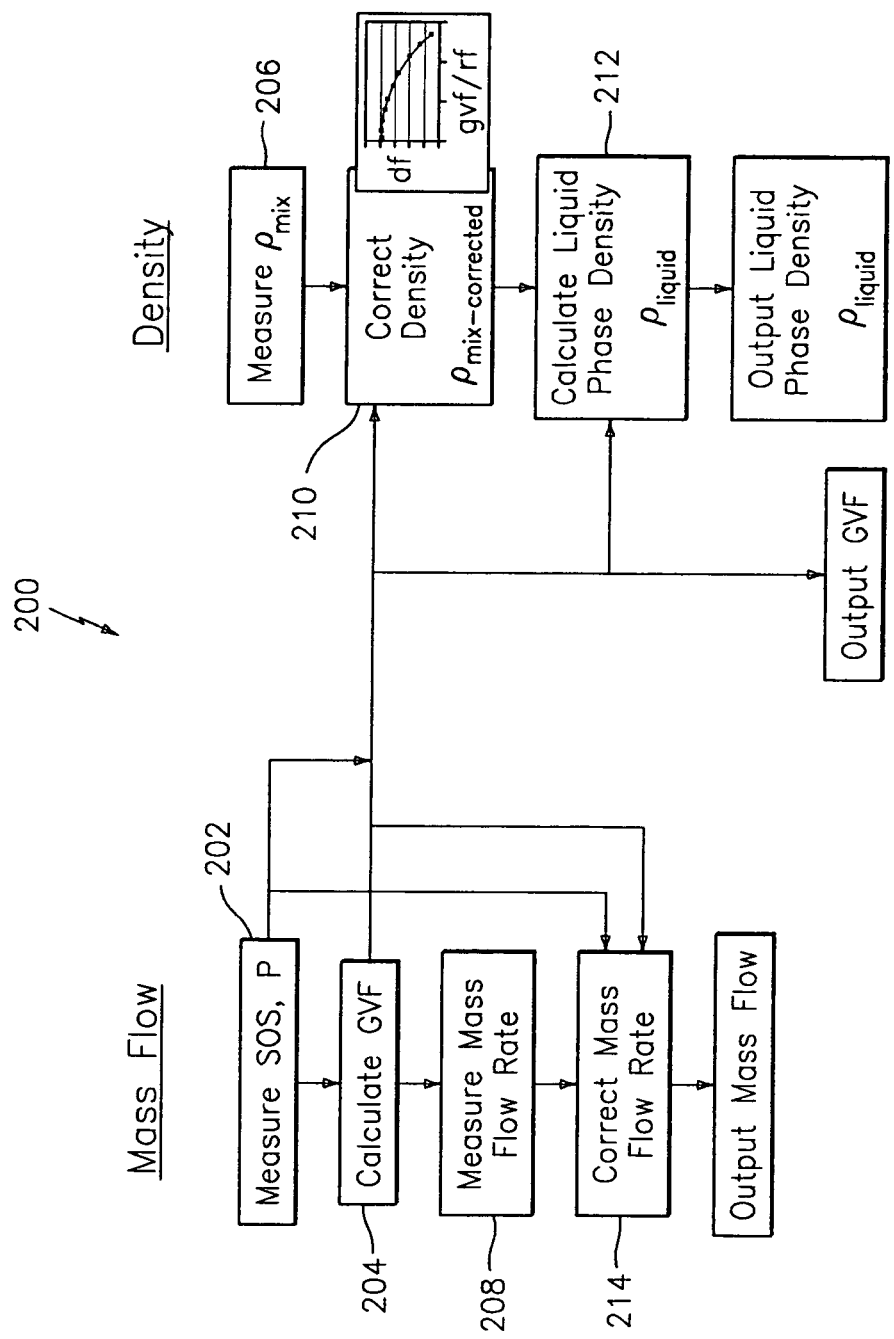
FIG. 2 is a flow chart illustrating a first embodiment of a method for measuring the mass flow and density of an aerated fluid flow using the well metering system of FIG. 1.
Figure 3:
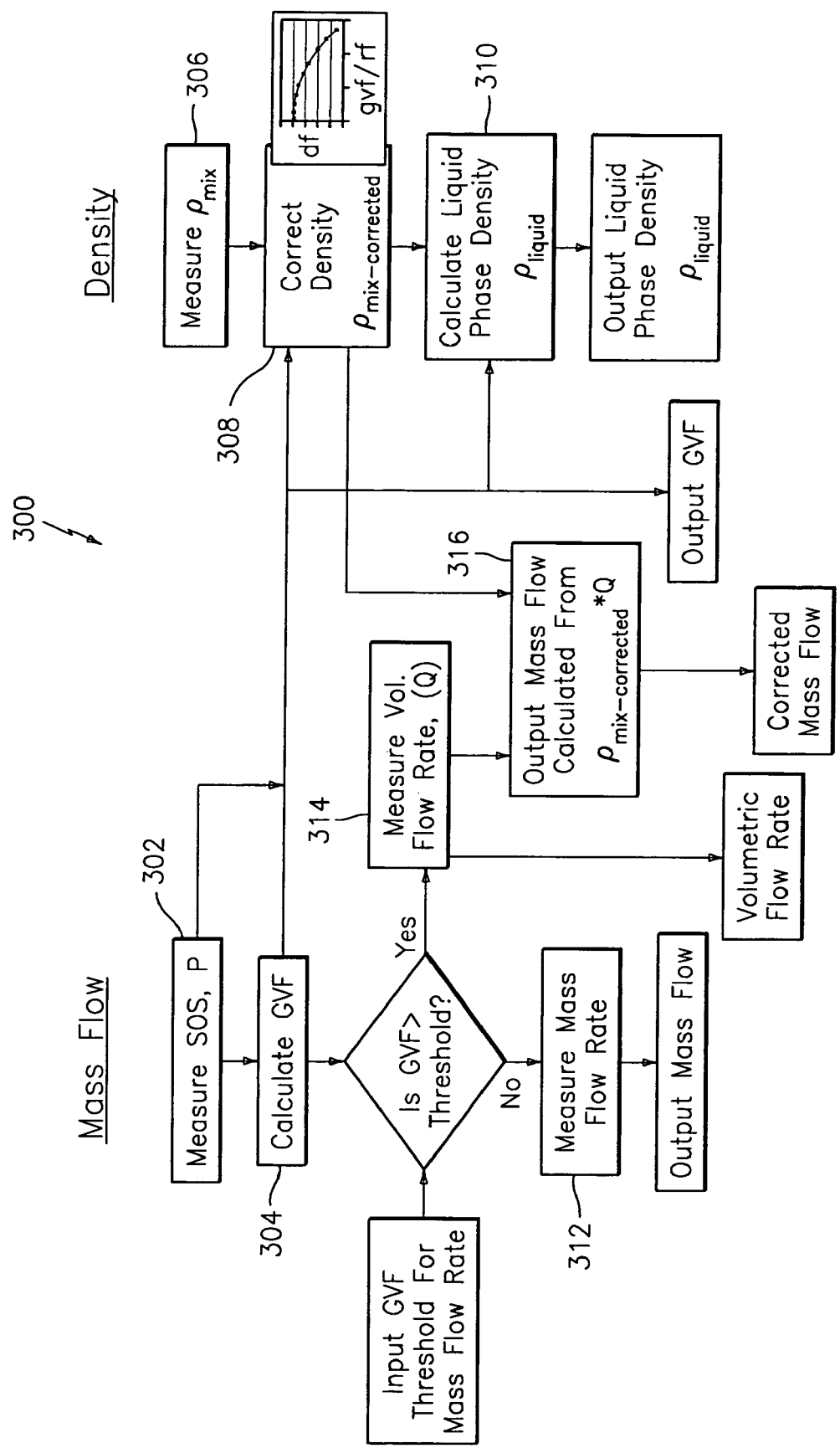
FIG. 3 is a flow chart illustrating a second embodiment of a method for measuring the mass flow and density of an aerated fluid flow using the well metering system of FIG. 1.

In accordance with the present invention, two processing methods for measuring the mass flow and density of the aerated fluid flow 108 are provided and illustrated in FIG. 2 and FIG. 3. Generally, the first method assumes that the performance of the density meter 122 for both the mass flow measurement and the density measurement can be augmented using the methods described in U.S. patent application Ser. No. 10/892,886 (CiDRA No. CC-0762), which is incorporated herein by reference. Referring to FIG. 2, a first embodiment of a method 200 for measuring the mass flow and density of an aerated fluid flow 108 may be described as follows. A production stream 102 is directed into the multiphase separator device 104, wherein the multiphase separator device 104 separates the production stream 102 into the first fluid flow 106 and the second fluid flow 108, wherein the first fluid flow 106 is comprised mostly of gas and wherein the second fluid flow 108 is comprised mostly of liquid. The second fluid flow 108 passes through the pipe 117. To determine the augmented density of the second fluid flow 108, the speed of sound (SOS) propagating through the second fluid flow 108 and the pressure (P) (and/or temperature) of the second fluid flow 108 are measured, as shown in operational block 202, and are used to calculate the gas volume fraction (GVF), as shown in operational block 204, as will be described in greater detail hereinafter. It should be appreciated that, if desired, a reduced frequency parameter of the density meter 122 may also be calculated for the second fluid flow 108. Additionally, the pressure (P) (and/or temperature) may be provided via a pressure sensor 126 (and/or temperature sensor 130) or the pressure (P) (and/or temperature) may be an estimated pressure (temperature) value.

Figure 4:
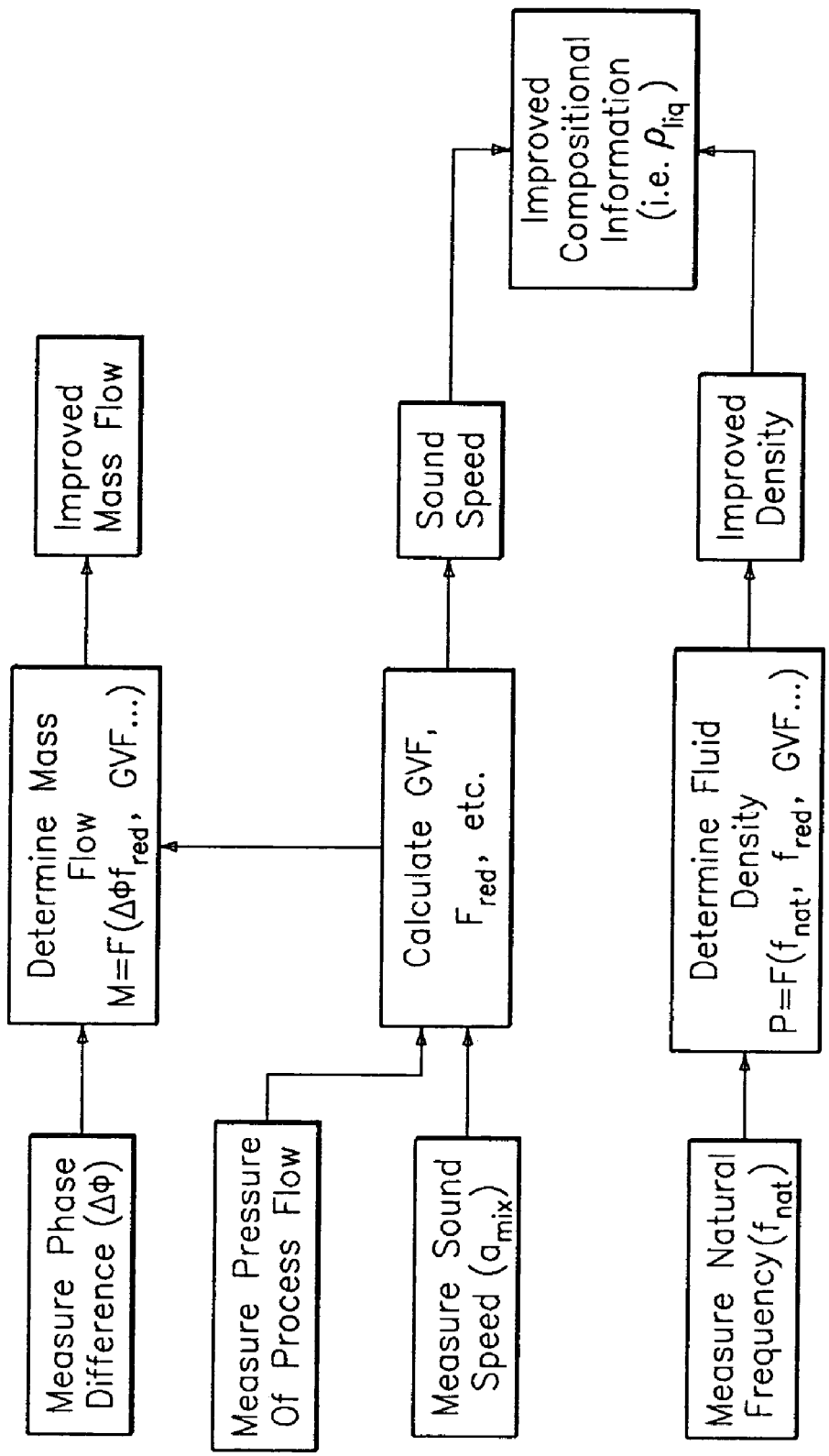
FIG. 4 is a functional block diagram of a processing unit of a well metering system of FIG. 1.

The density meter 122, such as a Coriolis meter, receives the second fluid flow 108 and measures the density ($\rho_{mix}$) and the mass flow rate ($MFR_{mix}$) of the second fluid flow, as shown in operational block 206 and operational block 208, respectively, as is known in the art. Using the speed of sound (SOS), the pressure (P) and the gas volume fraction (GVF), the density ($\rho_{mix\text{-}coriolis}$) of the second fluid flow 108 as measured by the Coriolis meter 122 may then be corrected to generate a corrected density ($\rho_{mix\text{-}corrected}$) which compensates for the effects of aeration as shown in operational block 210 and as discussed in more detail hereinafter (also as similar to that as described in U.S. patent application Ser. No. 10/892,886 (CiDRA No. CC-0762). As shown in FIG. 4, the liquid phase density ($\rho_{liquid}$) may then be calculated using the corrected density ($\rho_{mix\text{-}corrected}$) of the second fluid flow 108 and the gas volume fraction (GVF) of the second fluid flow and the gas density ($\rho_{gas}$), as shown in operational block 212. Additionally, using the speed of sound (SOS), the pressure (P) and the gas volume fraction (GVF), the mass flow rate ($MFR_{mix\text{-}coriolis}$) of the second fluid flow 108 as measured by the Coriolis meter 122 may then be used to correct the mass flow rate ($MFR_{mix\text{-}corrected}$) to compensate for any errors that may be present, as shown in operational block 214. At this point, the Coriolis mass flow, the GVF and the liquid phase density may then be outputted.

Referring to FIG. 3, a second embodiment of a method 300 for measuring the mass flow and density of an aerated fluid flow 108 may be described as follows. As discussed hereinabove, the production stream 102 is directed into the multiphase separator device 104, wherein the multiphase separator device 104 separates the gas portion of the production stream 102 from the liquid portion of the production stream 102. The multiphase separator device 104 directs the liquid portion through the pipe 117. The density of the second fluid flow 108 is determined by measuring the pressure and speed of sound ($SOS_{mix}$) through the second fluid flow 108, as shown in operational block 302. These values are then used to calculate the gas volume fraction (GVF) and/or a reduced frequency parameter of the Coriolis meter 122 operating on the second fluid flow 108, as shown in operational block 304. The speed of sound ($SOS_{mix}$) may be measured by the flow meter 120 and the pressure (P) provided by a pressure sensor 126 or the pressure (P) may be an estimated pressure value.

Figure 5:
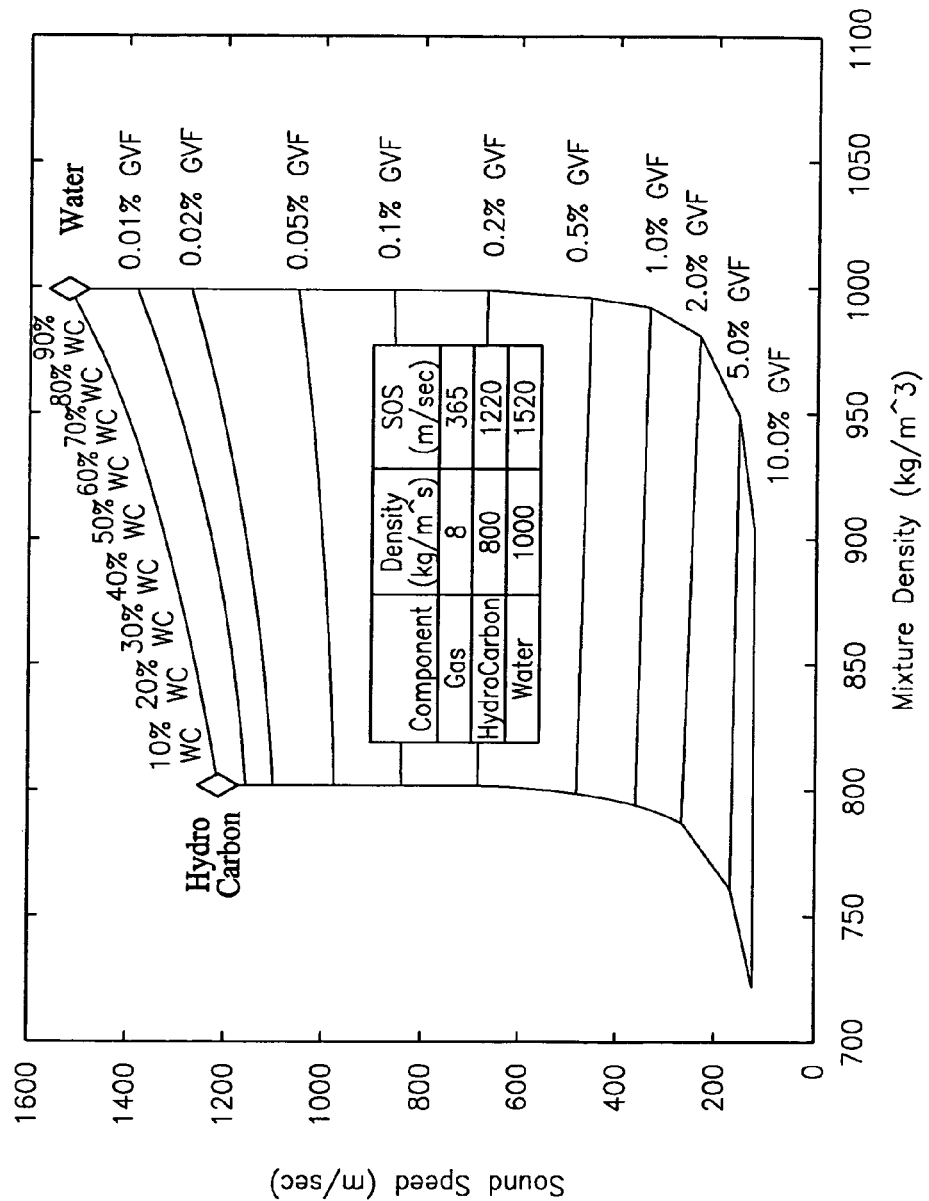
FIG. 5 is a plot illustrating the relationship between the Speed of Sound, the mixture density, the gas volume fraction and the liquid phase density.

The density meter 122, such as a Coriolis meter, receives the second fluid flow 108 and measures the density ($\rho_{mix}$) of the second fluid flow, as shown in operational block 306. Using the speed of sound ($SOS_{mix}$), the pressure (P) and the gas volume fraction (GVF), the density ($\rho_{mix}$) of the second fluid flow 108 as measured by the Coriolis meter 122 may then be corrected to generate a corrected density ($\rho_{mix\text{-}corrected}$) which compensates for the effects of aeration as discussed in more detail hereinafter (also as similar to that as described in U.S. patent application Ser. No. 10/892,886 (CiDRA No. CC-0762)), as shown in operational block 308. The mixture density ($\rho_{mix}$) may be determined by correcting the output of the Coriolis meter 122 for the effects of aeration similar to that as illustrated in FIG. 4. As shown in FIG. 5, the liquid phase density ($\rho_{liquid}$) may then be determined using the corrected density ($\rho_{mix\text{-}corrected}$) of the second fluid flow 108 along with the gas volume fraction (GVF) of the second fluid flow 108 and the gas density ($\rho_{gas}$), as shown in operational block 310.

Additionally, using the speed of Sound ($SOS_{mix}$), the pressure (P) and the gas volume fraction (GVF), the mass flow rate ($MFR_{mix}$) of the second fluid flow 108 as measured by the Density meter 122 may then be used to correct the mass flow rate ($MFR_{mix}$) to compensate for any errors that may be present. In accordance with the present invention, this may be accomplished via one of two methods, depending upon the value of the gas volume fraction (GVF) measurement of the flow meter 120. If the gas volume fraction (GVF) measurement is equal to or less than a predetermined GVF threshold value, then the mass flow rate is measured by the Coriolis meter 122, as shown in operational block 312, and may be used for future determinations. However, if the gas volume fraction (GVF) measurement is above the GVF threshold, then the mass flow rate is calculated by first determining the total mixture volumetric flow rate (Q) using the flow meter 120, as shown in operational block 314, as will be described in greater detail hereinafter, and then by multiplying this value by the corrected density mixture $\rho_{mix\text{-}corrected}$, as shown in operational block 316, to provide a corrected mass flow rate.

Referring to FIG. 6, a block diagram of the flow meter 120 includes a device for measuring the speed of sound (SOS) propagating through the fluid flow 108 within the pipe 117 and velocity of the fluid flow 108 through the pipe. A pressure sensor 126 and/or temperature sensor 130 may be used to measure the pressure (P) and/or temperature (T) of the fluid flow 108 flowing through the pipe 117. In response to the speed of sound signal and the characteristics of the fluid flow 108 (e.g., pressure, temperature), the processing device 124 may determine the gas volume fraction (GVF) of the fluid flow 108, wherein the pressure sensor 126 and/or the temperature sensor 130 enables the flow meter 120 to compensate or determine the gas volume fraction for any dynamic changes in the pressure and/or temperature of the fluid flow 108. Alternatively, the pressure and/or temperature may be estimated rather than actually measured.

Figure 7:
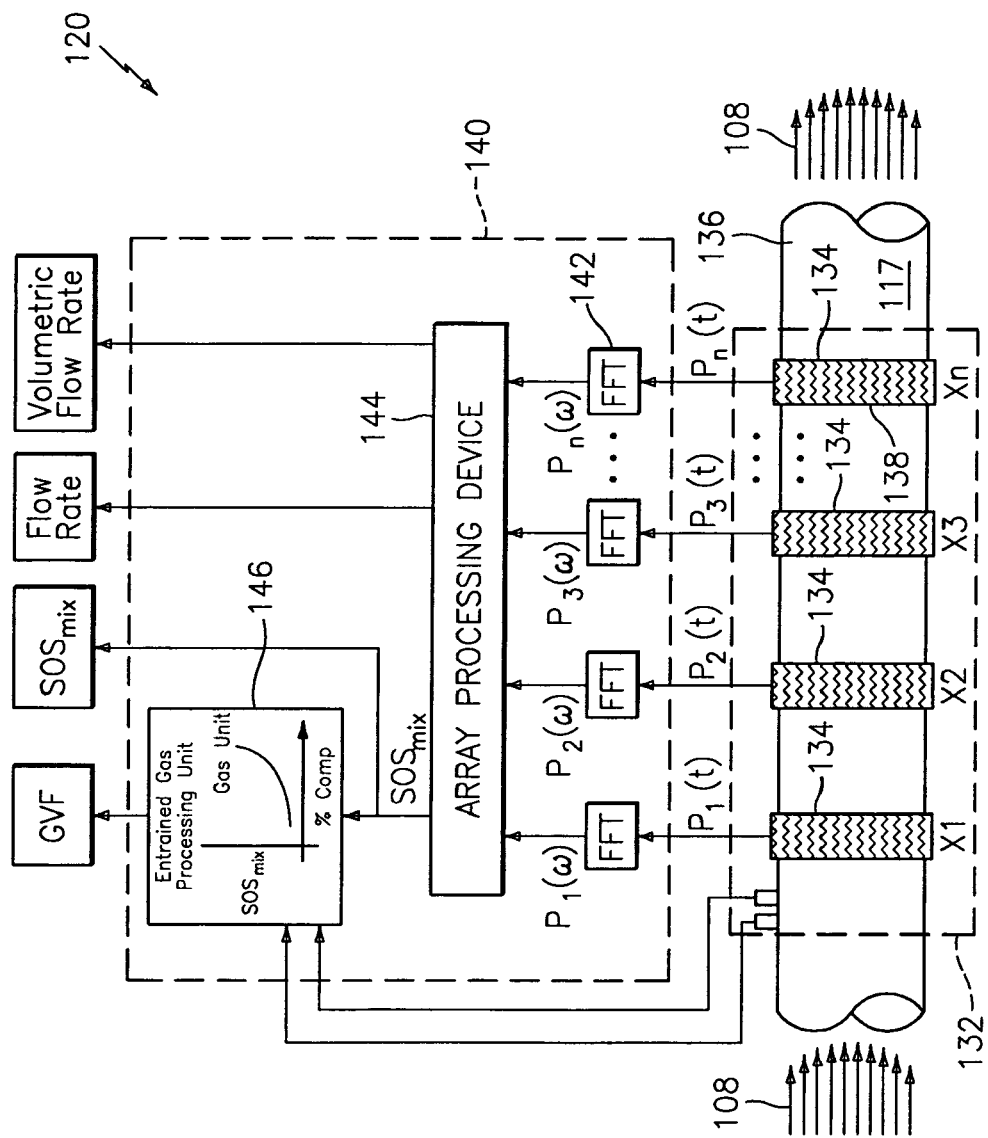
FIG. 7 is a side schematic diagram of a flow meter for the well metering system of FIG. 1.

FIG. 7 illustrates a schematic drawing of a flow meter 120 in accordance with the present invention, which includes a sensing device 132 comprising an array of pressure sensors (or transducers) 134 spaced axially along the outer surface 136 of a pipe 117, having a fluid flow 108 propagating therein. The pressure sensors 134 measure the unsteady pressures produced by acoustical disturbances within the pipe 112, which are indicative of the SOS propagating through the fluid flow 108 and pressure disturbances propagating with the fluid flow. The output signals ($P_1$-$P_N$) of the pressure sensors 134 are provided to the processor 124, which processes the pressure measurement data and determines the speed of sound, gas volume fraction (GVF), flow velocity and gas volume flow. It should be appreciated that that the flow meter 120 may have at least two pressure sensors 134 disposed axially along the pipe 117 for measuring the unsteady pressure $P_1$-$P_N$ of the fluid flow 108 flowing therethrough. The speed of sound propagating through the fluid flow 108 may be derived by interpreting the unsteady pressure field within the process piping 117 using multiple transducers displaced axially over ~2 diameters in length. The flow measurements can be performed using ported pressure transducers or clamp-on, strain-based sensors.

As discussed, the flow meter 120 has the ability to measure the gas volume fraction by determining the speed of sound of acoustical disturbances or sound waves propagating through the fluid flow 108 using the array of pressure sensors 134.

While the flow meter 120 shows at least four pressure sensors 134, it is contemplated that a flow meter 120 having an array of two or more pressure sensors 134 and having as many as sixteen (16) pressure sensors 134 may be used. Generally, the flow meter 120 measures unsteady pressures created by acoustical disturbances propagating through the fluid flow 108 to determine the speed of sound (SOS) propagating through the fluid flow. Knowing the pressure and/or temperature of the fluid flow 108 and the speed of sound of the acoustical disturbances, the processing device 124 can determine the gas volume fraction of the fluid flow 108, as described and shown in FIG. 8.

Moreover, the flow meter 120 also contemplates providing one or more acoustic sources to enable the measurement of the speed of sound propagating through the fluid flow 108 for instances of acoustically quiet flow. The acoustic source may be a device that taps or vibrates on the wall of the pipe 117, for example. The acoustic sources may be disposed at the input end or the output end of the array of sensors 134, or at both ends. One should appreciate that in most instances the acoustics sources are not necessary and the flow meter 120 passively detects the acoustic ridge provided in the fluid flow 108, wherein the passive noise may include noise generated by pumps, valves, motors, and the turbulent mixture itself.

The flow meter 120 may be configured and programmed to measure and process the detected unsteady pressures $P_1(t)$-$P_N(t)$ created by acoustic waves and pressure disturbances propagating through the fluid flow 108 to determine the SOS and flow velocity, respectively, through the fluid flow 108 in the pipe 117.

Referring again to FIG. 7, an example of one flow meter 120 that measures the speed of sound (SOS) of one-dimensional sound waves propagating through the mixture to determine the gas volume fraction of the mixture, and the pressure disturbances to determine the flow velocity is shown. The array processing unit includes flow logic and SOS logic to determine the flow velocity and speed of sound of the fluid, respectively.

The flow logic 166 of the processing unit 124 as shown in FIG. 10 receives the pressure signals from the array of sensors 160, 162. A data acquisition unit 168 (e.g., A/D converter) converts the analog signals to respective digital signals. The digitized signals are provided to Fast Fourier Transform (FFT) logic 170. The FFT logic 170 calculates the Fourier transform of the digitized time-based input signals $P_1(t)$-$P_N(t)$ and provides complex frequency domain (or frequency based) signals $P_1(\omega)$, $P_2(\omega)$, $P_3(\omega)$, $P_N(\omega)$ indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

One technique of determining the convection velocity of the turbulent eddies 164 within the fluid stream 108 is by characterizing a convective ridge of the resulting unsteady pressures using an array of sensors or other beam forming techniques, similar to that described in U.S. patent application, Ser. No. 10/007,736 and U.S. patent application Ser. No. 09/729,994, filed Dec. 4, 200, now U.S. Pat. No. 6,609,069, which are incorporated herein by reference.

A data accumulator 172 accumulates the frequency signals $P_1(\omega)$-$P_N(\omega)$ over a sampling interval, and provides the data to an array processor 174, which performs a spatial-temporal (two-dimensional) transform of the sensor data, from the x(t) domain to the k-$\omega$ domain, and then calculates the power in the k-$\omega$ plane, as represented by a k-$\omega$ plot.

The array processor 174 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

The prior art teaches many algorithms of use by spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,$$

wherein u is the convection velocity (flow velocity). A plot of k-$\omega$ pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 164 are distributed over a range of length scales and hence temporal frequencies.

Figure 12:
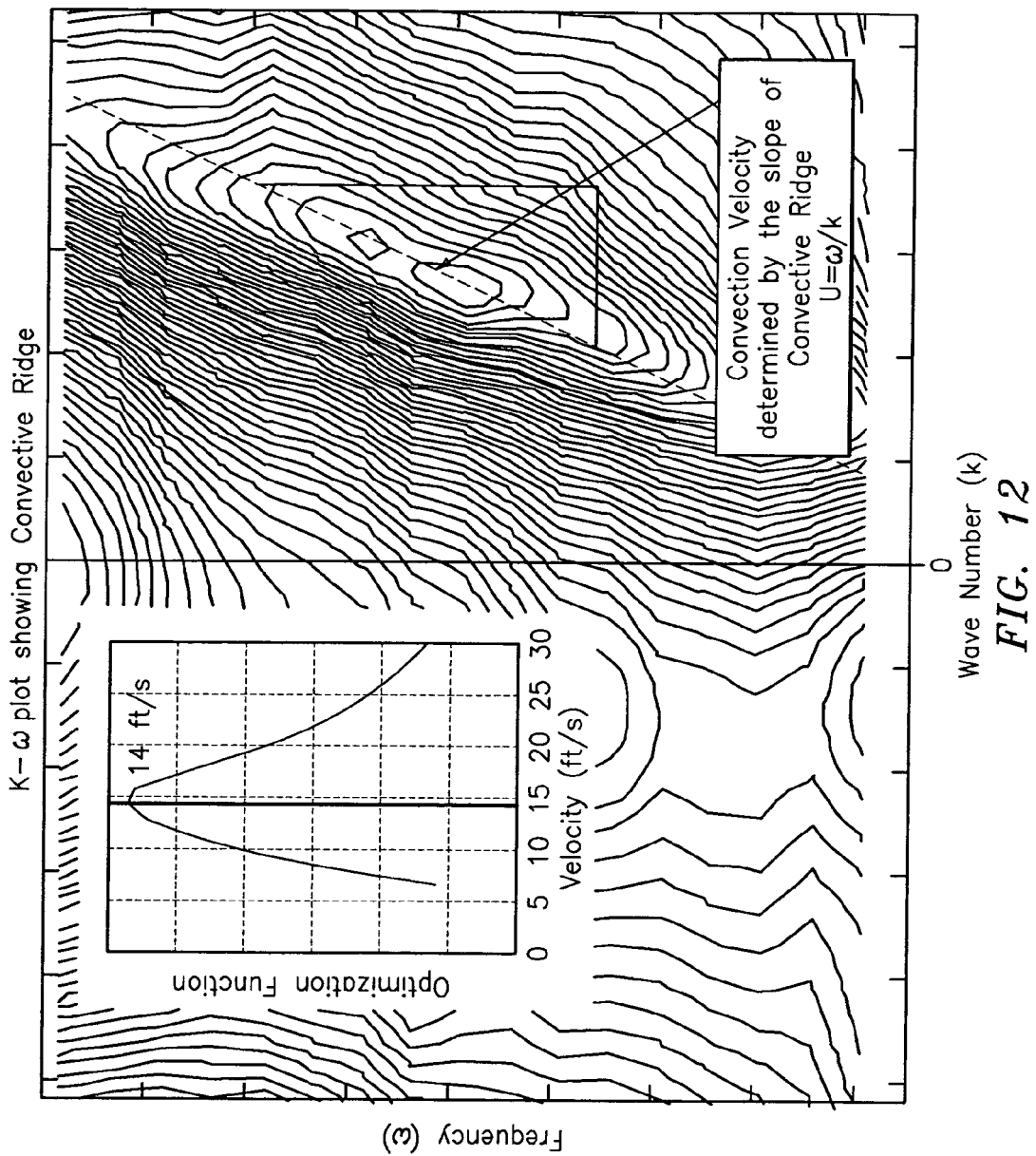
FIG. 12 is a kω plot of data processed from an apparatus embodying the present invention that illustrates the slope of a convective ridge, and a plot of the optimization function of the convective ridge, in accordance with the present invention.

To calculate the power in the k-$\omega$ plane, as represented by the k-$\omega$ plot in FIG. 12 of either the signals, the array processor 174 determines the wavelength and so the (spatial) wave number k, and also the (temporal) frequency and so the angular frequency $\omega$, of various of the spectral components of the stochastic parameter. There are numerous algorithms available in the public domain to perform the spatial/temporal decomposition of arrays of sensor units 160, 162.

The present invention may use temporal and spatial filtering to precondition the signals to effectively filter out the common mode characteristics $P_{common\ mode}$ and other long wavelength (compared to the sensor spacing) characteristics in the pipe 117 by differencing adjacent sensors and retain a substantial portion of the stochastic parameter associated with the flow field and any other short wavelength (compared to the sensor spacing) low frequency stochastic parameters.

In the case of suitable turbulent eddies 164 (see FIG. 9) being present, the power in the k-$\omega$ plane shown in a k-$\omega$ plot of FIG. 12 shows a convective ridge 176. The convective ridge represents the concentration of a stochastic parameter that convects with the flow and is a mathematical manifestation of the relationship between the spatial variations and temporal variations described above. Such a plot will indicate a tendency for k-ω pairs to appear more or less along a line 176 with some slope, the slope indicating the flow velocity.

Once the power in the k-ω plane is determined, a convective ridge identifier 180 uses one or another feature extraction method to determine the location and orientation (slope) of any convective ridge 176 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 180 provides information about the different trial convection velocities, information referred to generally as convective ridge information.

The analyzer 182 examines the convective ridge information including the convective ridge orientation (slope). Assuming the straight-line dispersion relation given by k=ω/u, the analyzer 182 determines the flow velocity, Mach number and/or volumetric flow. The volumetric flow is determined by multiplying the cross-sectional area of the inside of the pipe with the velocity of the process flow.

As shown in FIG. 11, the SOS logic 167 includes a second data acquisition unit 184 that digitizes the pressure signals $P_1(t)$-$P_N(t)$ associated with the acoustic waves 186 propagating through the pipe 117. Similarly to the FFT logic 170, an FFT logic 188 calculates the Fourier transform of the digitized time-based input signals $P_1(t)$-$P_N(t)$ and provide complex frequency domain (or frequency based) signals $P_1(\omega)$, $P_2(\omega)$, $P_3(\omega)$, $P_N(\omega)$ indicative of the frequency content of the input signals. However, it should be appreciated that instead of FFT's, any other technique for obtaining the frequency domain characteristics of the signals $P_1(t)$-$P_N(t)$, may be used. For example, the cross-spectral density and the power spectral density may be used to form a frequency domain transfer function (or frequency response or ratios) discussed hereinafter.

A data accumulator 190 accumulates the signals $P_1(t)$-$P_N(t)$ from the sensors, and provides the data accumulated over a sampling interval to an array processor 192, which performs a spatial-temporal (two-dimensional) transform of the sensor data, from the xt domain to the k-ω domain, and then calculates the power in the k-ω plane, as represented by a k-ω plot, similar to that provided by the convective array processor 174.

To calculate the power in the k-ω plane, as represented by a k-ω plot (see FIG. 13) of either the signals or the differenced signals, the array processor 192 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of the array of pressure sensors 160, 162.

Figure 13:
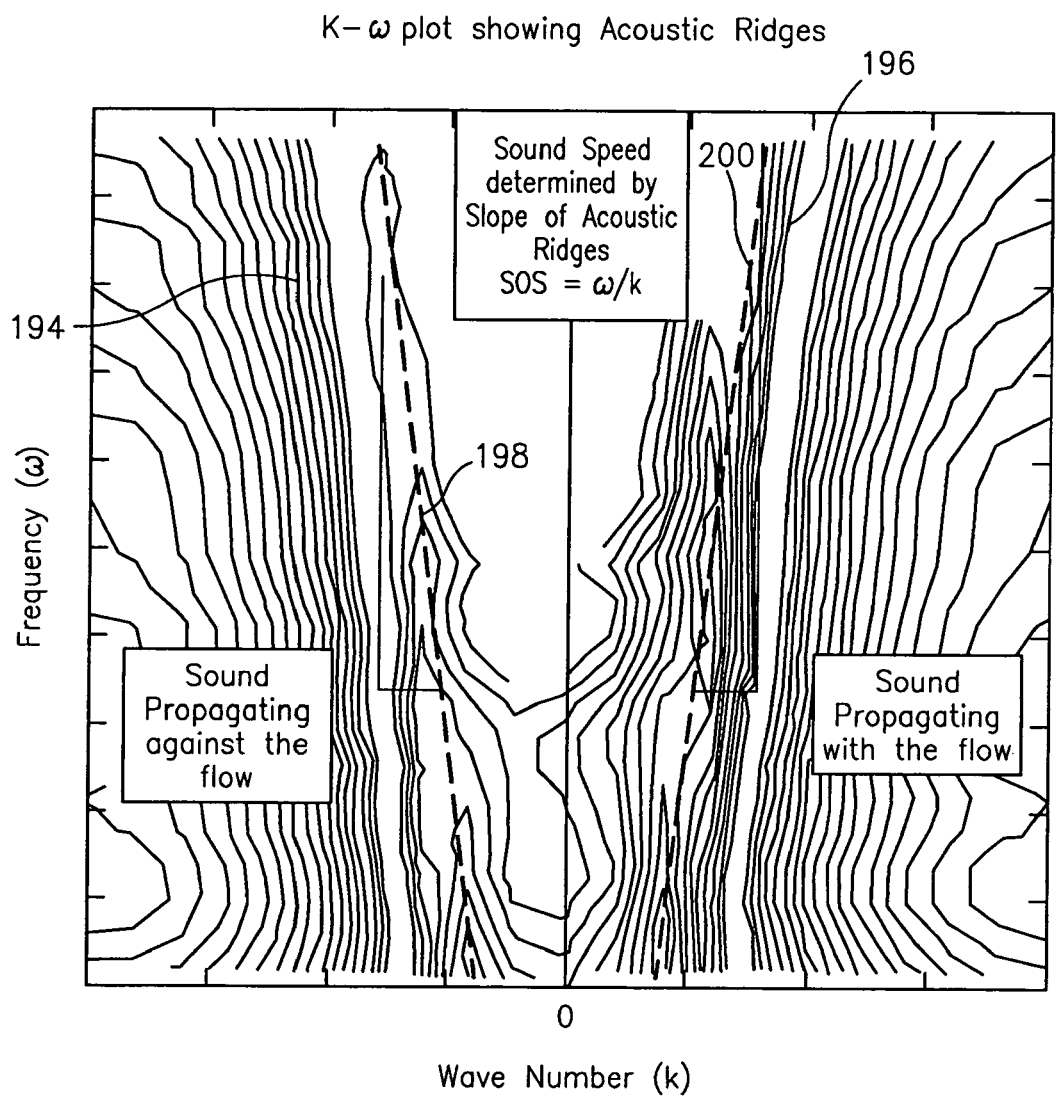
FIG. 13 is a kω plot of data processed from an apparatus embodying the present invention that illustrates the slopes of a pair of acoustic ridges, in accordance with the present invention.

In the case of suitable acoustic waves 186 being present in both axial directions, the power in the k-ω plane shown in a k-ω plot of FIG. 13 so determined will exhibit a structure that is called an acoustic ridge 194, 196 in both the left and right planes of the plot, wherein one of the acoustic ridges 194 is indicative of the speed of sound traveling in one axial direction and the other acoustic ridge 196 being indicative of the speed of sound traveling in the other axial direction.

The acoustic ridges 194, 196 represent the concentration of a stochastic parameter that propagates through the flow and is a mathematical manifestation of the relationship between the spatial variations and temporal variations described above. Such a plot will indicate a tendency for k-ω pairs to appear more or less along a line 198, 200 with some slope, the slope indicating the speed of sound. The power in the k-ω plane so determined is then provided to an acoustic ridge identifier 202, which uses one or another feature extraction method to determine the location and orientation (slope) of any acoustic ridge present in the left and right k-ω plane. The velocity may be determined by using the slope of one of the two acoustic ridges 194, 196 or averaging the slopes of the acoustic ridges 194, 196.

Finally, information including the acoustic ridge orientation (slope) is used by an analyzer 204 to determine the flow parameters 206 relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

Similar to the array processor 174, the array processor 192 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where λ is the wavelength of a spectral component, and corresponding angular frequencies given by $\omega=2\pi\nu$.

One such technique of determining the speed of sound propagating through the fluid stream 108 is by using array processing techniques to define an acoustic ridge in the k-ω plane as shown in FIG. 13. The slope of the acoustic ridge is indicative of the speed of sound propagating through the fluid flow 108. The speed of sound (SOS) is determined by applying sonar arraying processing techniques to determine the speed at which the one dimensional acoustic waves propagate past the axial array of unsteady pressure measurements distributed along the pipe 117.

The flow meter 120 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe 117 and fluid stream 108 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

Figure 8:
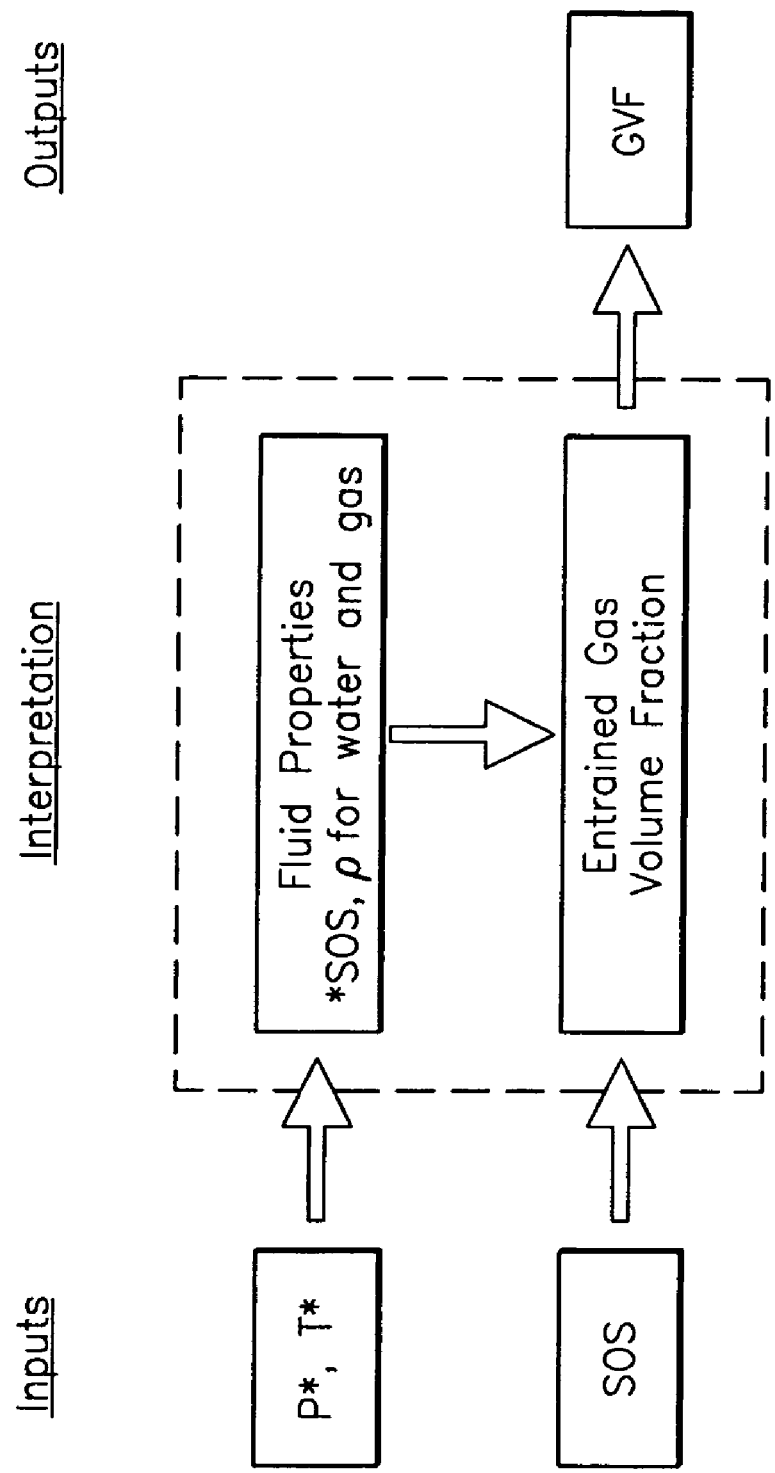
FIG. 8 is a block diagram of a process for determining gas volume fraction for the flow meter used with the well metering system of FIG. 1.

While the sonar-based flow meter using an array of sensors to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore. As shown in FIGS. 7 and 8, knowing the SOS of the mixture or fluid flow 108, the entrained gas processing unit determines the gas volume fraction of the fluid flow.

The array processing unit uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine speed of sound propagating through the fluid flow 108.

Also, some or all of the functions within the processor 124 may be implemented in software (using a microprocessor or computer) and/or firmware, or may be implemented using analog and/or digital hardware, having sufficient memory, interfaces, and capacity to perform the functions described herein.

It is within the scope of the present invention that the pressure sensor 134 spacing may be known or arbitrary and that as few as two sensors are required if certain information is known about the acoustic properties of the fluid flow 108. The pressure sensors 134 are spaced sufficiently such that the entire length of the array (aperture) is at least a significant fraction of the measured wavelength of the acoustic waves being measured. The acoustic wavelength is a function of the type or characteristics of the fluid flow 108.

Referring to FIG. 2, it should be appreciated that the corrected mass flow rate may be calculated, as shown in 214, using the method described in U.S. patent application Ser. No. 10/892,886 (CiDRA No. CC-0762)). One method to do this is to use the sound-speed based gas volume fraction parameter, a reduced frequency parameter relating to phase lag to mass flow rate. If the reduced frequency based on diameter is non-negligible, the inertial load from the fluid on the pipe 117 develops a slight phase lag that increases with increasing frequency. For non-negligible reduced frequencies based on the length of the flow tube, oscillations in the flow velocity can vary over the length of the pipe 117, potentially introducing error in the output of the meter.

As shown, typical variations in mixture sound speeds due to two phase flow result in significant variations in reduced frequencies. Thus, by dramatically reducing the mixture speed of sound, the introduction of gas to a liquid mixture can dramatically increase the reduced frequency of the primary vibration associated with the Coriolis meter 122. If not accounted for in the interpretation, this increase in reduced frequency renders the quasi-steady model increasingly inaccurate, and results in errors in mass flow and in density. This decrease in the accuracy of Corilois meter 122 with the introduction of bubbly fluids is well documented. In fact, others have attempted to correct for the effect of entrained air by correlating observed errors in mass flow to the gas volume fraction within the process fluid. These authors proposed a correction based on GVF as follows:

$$R = \frac{2\alpha}{1-\alpha}$$

Where the $\alpha$ represents the gas volume fraction and R represents the decrease in measured (apparent) mass flow normalized by the true mass flow. Thus, using this correlation, a 1% increase in entrained air would result in a roughly 2% underestimate of the actual mass flow.

What is proposed in this disclosure is to use a direct sound measurement from the process fluid to aid in the interpretation of the coriolis meter 122. In this interpretation, the reduced frequency parameters developed herein is included in interpreting the relationship between the phase difference in the vibrating tubes and the mass flow as well as a direct role in interpreting the natural frequency of the oscillating flow tubes in terms of process fluid density. The sound speed measurement, combined with knowledge of process liquid and gas components as well as process temperature and pressure, enables a direct measurement of entrained air as well. Thus, the reduced frequency parameter and gas volume fraction (GVF) can be used as inputs in the interpretation of phase lag in terms of the mass flow.

Due to the strong relationship between the air content in liquids and the mixture sound speed, the role of the reduced frequency parameter in the interpretation of the fundamental measurement of the Coriolis meter 122 will have a more pronounce effect in bubbly flows. However, changes in sound speed and hence reduced frequency of operation in various types of liquids and other process mixtures have an effect on the interpretation and hence the accuracy of the Coriolis meter 122 used in these applications as well. Consider, flow example, the performance of the Coriolis meter 122 on two liquids—water and oil. Assume that the fluids have different densities and sound speeds. The different fluid properties suggest that the Coriolis meters 122 will be operating at different reduced frequencies. The reduced frequency for the water will typically be ~10%-30% lower than that for the oil application.

Figure 14:
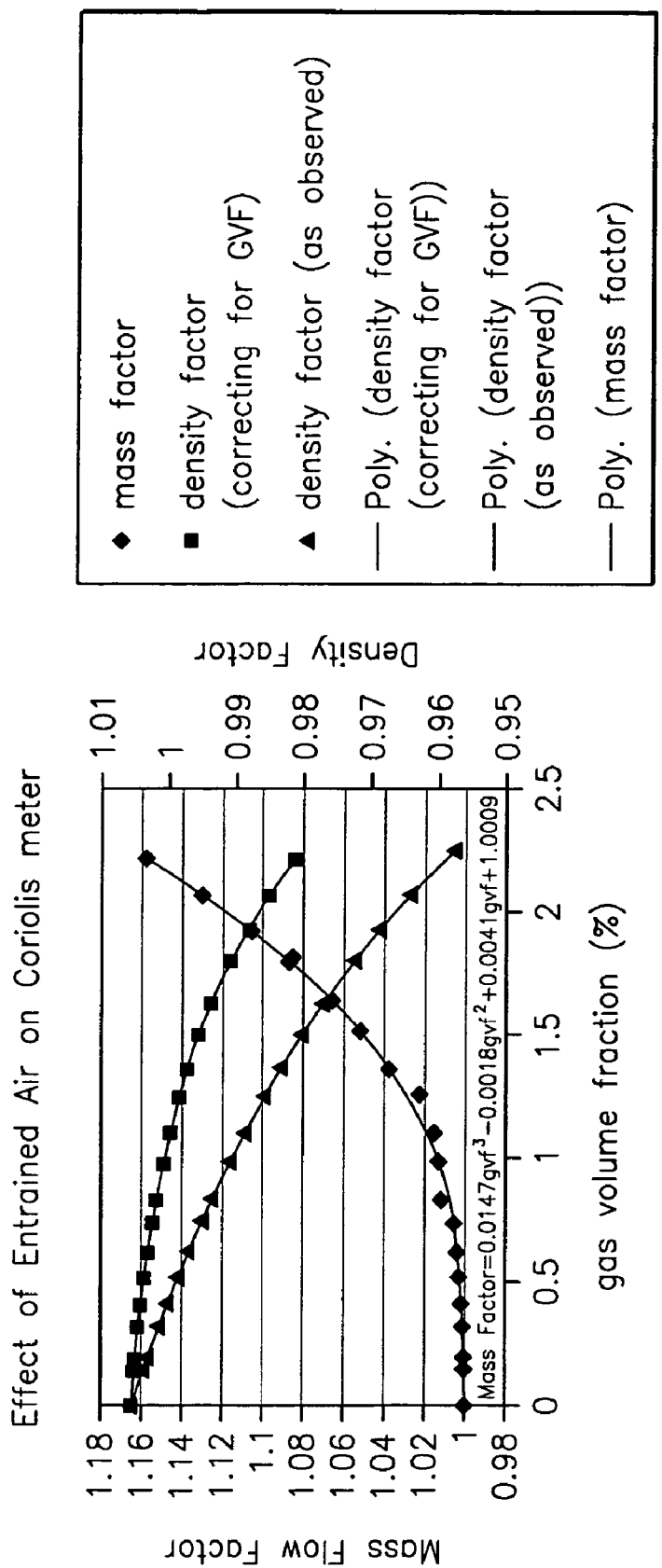
FIG. 14 is a plot of the density factor and mass flow factor as a function of the gas volume fraction, in accordance with the present invention.

Recognizing that, while they are different, the reduced frequencies for both applications are still "small", the impact on accuracy may not be significant. However, some degree of inaccuracy is introduced by not accounting for the differences in the reduced frequency of operation of the Coriolis meter 122 in this application. The errors associated with the Coriolis meter 1222 operating in the aerated liquids can be determined and plotted as a function of sound speed based parameters. The Coriolis meter 1222 performance may be characterized as a function of gas volume fraction (GVF), wherein the errors in mass flow, mixture density, and observed mixture density are shown in FIG. 14. For this example, the mass flow error is parameterized by the sound speed-based gas volume fraction of entrained air. The parametric dependence of this is given by the equation shown on the plot.

Mass Factor=$0.0147gvf^3-0.0018gvf^2+0.0041gvf+1.0009$

Referring to FIG. 14, a density factor related to the relationship of (1-GVF) is shown to provide a correction factor to correct for density of an aerated fluid flow as shown in block 308 in FIG. 3.

As shown in FIG. 3 block 310, the present invention further contemplates determining improved compositional information of the aerated flow. In other words, knowing the speed of sound propagating through the flow and the improved density, the processing unit 21 can determine density of the fluid/mixture portion of the multiphase flow.

For example, the density ($\rho_{mix}$) of an aerated flow is related to the volumetric phase fraction of the components ($\phi_i$) and the density of the components ($\rho_i$).

$$\rho_{mix} = \sum_{i=1}^{N} \phi_i \rho_i$$

Where continuity requires:

$$\sum_{i=1}^{N} \phi_i = 1$$

The system 10 provides an improved measure of the density of the aerated flow. For a two-component mixture, knowing the density ($\rho_{gas}$), gas volume fraction (or SOS) and accurately measuring the mixture density ($\rho_{mix}$) provides a means to determine the density ($\rho_{nongas}$) of the non-gas portion of the fluid flow. For example, for a two-component fluid flow:

$$\rho_{mix} = \rho_{nongas}\phi_{nongas} + \rho_{gas}\phi_{gas}$$

therefore, $\rho_{nongas} = (\rho_{mix} - \rho_{gas}\phi_{gas})/\phi_{nongas}$, wherein $\phi_{nongas} = 1 - \phi_{gas}$ wherein $\rho_{mix}$ is the density of the mixture, $\rho_{nongas}$, $\phi_{nongas}$ are the density and phase fraction, respectively, of a non-gas component of the fluid flow, and $\rho_{gas}$, $\phi_{gas}$ are the density and phase fraction, respectively, of the entrained gas within the mixture.

Therefore, knowing the density ($\rho_{gas}$) of the gas/air, the measured gas volume fraction of the gas ($\phi_{gas}$), and the improved density measurement ($\rho_{mix}$) of the aerated flow to be compensated for entrained gas enable the density ($\rho_{nongas}$) of the non-gas portion of the aerated flow 12 to be determined, which provides improved compositional information of the aerated flow 12.

Figure 15:
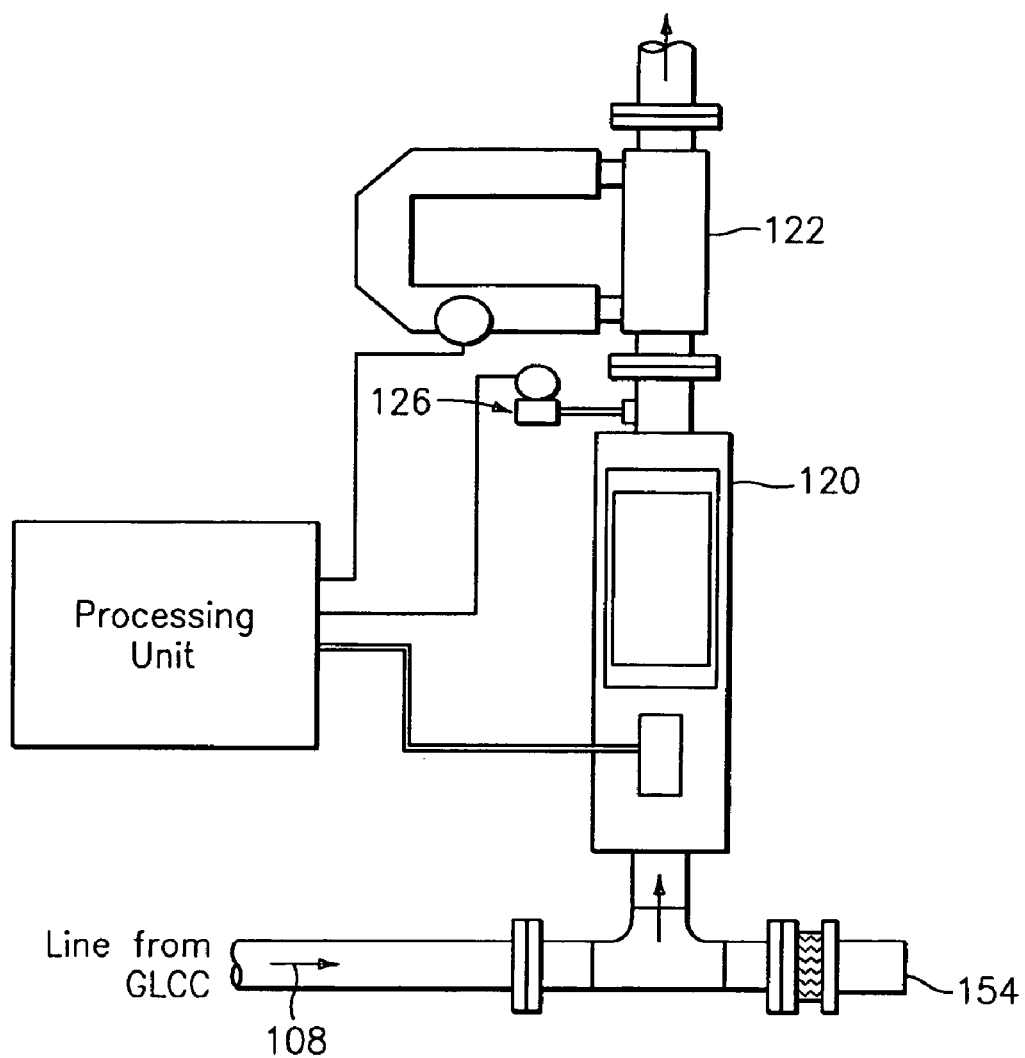
FIG. 15 is an additional embodiment of a well metering device with the flow meter and the density meter vertically installed.

Referring to FIG. 15, an additional embodiment of the present invention is shown wherein the flow meter 120 and the density meter 122, such as the Coriolis meter, are disposed in a vertical position to reduce or eliminate stratification of the gas within the aerated fluid. It should be appreciated that although this embodiment is shown as having a low-frequency active acoustic (noise) source 154, the invention contemplates no need for a noise source provided a sufficient level of acoustic noise is propagating through the fluid flow 108. Moreover, while a Coriolis meter 122 is shown to measure density, the invention contemplates that any density meter may be used, such as a gamma densitometer. The Coriolis meter 122 may also have bent tubes or straight tubes.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein. While the invention has been described with reference to an exemplary embodiment, it should be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A flow measuring system for determining a characteristic of a fluid flowing within a pipe, the flow measuring system comprising:
    a flow meter device, wherein said flow meter device is disposed to receive the fluid flow, wherein said flow meter device generates flow data responsive to at least one characteristic of the fluid flow;
    a density meter, wherein said density meter is in flow communication with said flow meter device to receive the fluid flow, wherein said density meter generates density data responsive to said at least one characteristic of the fluid flow; and
    a processing device, wherein said processing device is communicated with at least one of said flow meter device and said density meter to receive said flow data and said density data, wherein said processing device determines said at least one characteristic of the fluid flow.

2. The flow measuring system of claim 1, wherein said characteristic includes at least one of Gas Volume Fraction, Volumetric Flow Rate, Mass Flow Rate, Corrected Mass Flow Rate, Corrected Liquid Density and Mixture Density.

3. The flow measuring system of claim 1, wherein said density data includes at least one of mass flow rate and density of the fluid.

4. The flow measuring system of claim 1, wherein said flow data includes at least one of a volumetric flow rate, Gas Volume Fraction and Speed of Sound through the fluid.

5. The flow measuring system of claim 1, where said flow meter device includes an array of strain sensors.

6. The flow measuring system of claim 1, wherein the flow measuring system includes at least one of a pressure sensing device and a temperature sensing device associated with the fluid flow.

7. The flow measuring system of claim 1, wherein said flow meter device and said density meter device are in fluid communication with a separation device liquid output of a separation device.

8. The flow measuring system of claim 7, wherein said separation device is a cyclone separator device.

9. The flow measuring system of claim 1, wherein said flow meter device are non-intrusively associated with the flow measuring system.

10. The flow measuring system of claim 1, wherein said flow meter device and said density meter are disposed in a vertical fashion to prevent stratification.

11. A method for measuring at least one characteristic of an aerated fluid flowing within a pipe, the method comprising:
    generating a measured sound speed, a measured density, a pressure and a Gas Volume Fraction for the aerated fluid;
    correcting said measured density responsive to said measured sound speed, said pressure and said Gas Volume Fraction to generate a corrected density;
    calculating a liquid phase density responsive to said corrected density, said measured sound speed, said pressure and said Gas Volume Fraction;

generating a measured a mass flow rate responsive to said Gas Volume Fraction; and correcting said measured mass flow rate responsive to said measured sound speed, said pressure and said Gas Volume Fraction to generate a corrected mass flow rate.

12. The method of claim 11, wherein the characteristic of the flowing aerated fluid is at least one of a liquid density, a Gas Volumetric Fraction, a volumetric flow rate, a mass flow rate, a corrected density and a mixture density.

13. The method of claim 11, wherein said generating includes at least one of generating a measured speed of sound via a flow meter and generating a measured density via a Coriolis meter.

14. The method of claim 11, wherein said pressure is at least one of a measured pressure value and an estimated pressure value.

15. The method of claim 11, wherein said generating a measured mass flow rate includes measuring a mass flow rate via said density meter.

16. A method for measuring at least one characteristic of an aerated fluid flowing within a pipe, the method comprising:

generating a measured sound speed, a measured density, a pressure and a Gas Volume Fraction for the aerated fluid;

calculating a Gas Volume Fraction responsive to said measured sound speed and said pressure;

correcting said measured density responsive to said measured sound speed, said pressure and said Gas Volume Fraction to generate a corrected density;

calculating a liquid phase density;

determining whether said Gas Volume Fraction is greater than a predetermined threshold value; and generating a mass flow rate responsive to whether said gas volume fraction is greater than said predetermined threshold value.

17. The method of claim 16, wherein the characteristic of the flowing aerated fluid is at least one of a liquid density, a Gas Volumetric Fraction, a volumetric flow rate, a mass flow rate, a corrected density and mixture density.

18. The method of claim 16, wherein said generating includes at least one of generating a measured speed of sound via a flow meter and generating a measured density via a Coriolis meter.

19. The method of claim 16, wherein said pressure is at least one of a measured pressure value and an estimated pressure value.

20. The method of claim 16, wherein if said Gas Volume Fraction is equal to or less than said predetermined threshold value, said generating a mass flow rate includes measuring the mass flow rate via said density meter.

21. The method of claim 16, wherein if said Gas Volume Fraction is greater than said predetermined threshold value, said generating a mass flow rate includes measuring a volumetric flow rate via said flow meter and multiplying said volumetric flow rate with said corrected density.

* * * * *